United States Patent
Sterrantino et al.

(10) Patent No.: US 10,342,452 B2
(45) Date of Patent: Jul. 9, 2019

(54) STIMULATOR HANDPIECE FOR AN EVOKED POTENTIAL MONITORING SYSTEM

(75) Inventors: Peter P. Sterrantino, Wyckoff, NJ (US); David C. Hacker, Jacksonville, FL (US); Bret M. Berry, Sandy, UT (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 2710 days.

(21) Appl. No.: 10/901,933

(22) Filed: Jul. 29, 2004

(65) Prior Publication Data
US 2006/0025702 A1    Feb. 2, 2006

(51) Int. Cl.
  A61B 5/05       (2006.01)
  A61N 1/36       (2006.01)
  A61B 5/0484     (2006.01)
  A61B 5/0488     (2006.01)

(52) U.S. Cl.
  CPC .............. *A61B 5/05* (2013.01); *A61B 5/0488* (2013.01); *A61B 5/0484* (2013.01); *A61N 1/36014* (2013.01)

(58) Field of Classification Search
  CPC ....... A61B 5/05; A61B 5/0488; A61B 5/0484; A61N 1/36014
  USPC ................ 600/554, 443–447, 459, 300, 373; 607/48, 63, 62
  See application file for complete search history.

(56) References Cited

U.S. PATENT DOCUMENTS

| | | | |
|---|---|---|---|
| 3,219,029 A | | 11/1965 | Richards et al. |
| 4,503,842 A | * | 3/1985 | Takayama ............ A61B 1/0052 200/6 A |
| 4,515,168 A | | 5/1985 | Chester et al. |
| 5,347,989 A | * | 9/1994 | Monroe et al. ............... 600/131 |
| 5,373,317 A | * | 12/1994 | Salvati ............... A61B 1/00052 348/65 |
| 5,540,235 A | * | 7/1996 | Wilson .......................... 600/554 |
| 5,687,080 A | * | 11/1997 | Hoyt et al. ...................... 700/85 |
| 5,775,331 A | | 7/1998 | Raymond et al. |
| 5,806,522 A | * | 9/1998 | Katims ............... G06F 19/3481 600/554 |
| 5,836,880 A | * | 11/1998 | Pratt ............................. 600/443 |
| 5,857,986 A | * | 1/1999 | Moriyasu ............... A61H 23/02 273/148 B |

(Continued)

OTHER PUBLICATIONS

PCT Search Report dated Dec. 1, 2005 (9 pgs).

*Primary Examiner* — Rene T Towa
(74) *Attorney, Agent, or Firm* — Dicke, Billig & Czaja, PLLC

(57) ABSTRACT

An evoked potential monitoring system including a control unit having stimulator circuitry and a probe assembly coupled to the control unit. The probe assembly includes a stimulus probe and a stimulator handpiece selectively coupled to the stimulus probe. The handpiece includes a handle, control circuitry, and a switch. The control circuitry is electrically coupled to the stimulator circuitry. The switch is electrically coupled to the control circuitry and extends to an exterior portion of the handle. In this regard, movement of the switch remotely controls the stimulator circuitry to continuously increment or decrement a stimulation energy level delivered to the stimulus probe over a series of discrete, incremental steps.

27 Claims, 10 Drawing Sheets

(56) References Cited

U.S. PATENT DOCUMENTS

| | | | |
|---|---|---|---|
| 5,954,716 A * | 9/1999 | Sharkey | A61B 18/148 606/32 |
| 6,139,545 A | 10/2000 | Utley et al. | |
| 6,146,334 A * | 11/2000 | Laserow | A61B 5/4824 600/552 |
| 6,249,706 B1 * | 6/2001 | Sobota et al. | 607/115 |
| 6,292,701 B1 * | 9/2001 | Prass et al. | 607/116 |
| 6,314,324 B1 * | 11/2001 | Lattner et al. | 607/42 |
| 6,618,626 B2 * | 9/2003 | West, Jr. | A61B 18/148 606/34 |
| 7,363,079 B1 * | 4/2008 | Thacker et al. | 607/27 |
| RE44,049 E * | 3/2013 | Herzon | 600/554 |
| 2001/0049524 A1 * | 12/2001 | Morgan | A61B 18/148 606/50 |
| 2002/0065481 A1 * | 5/2002 | Cory | A61N 1/36021 604/21 |
| 2002/0149384 A1 * | 10/2002 | Reasoner | 324/761 |
| 2002/0193779 A1 * | 12/2002 | Yamazaki et al. | 606/9 |
| 2003/0088185 A1 * | 5/2003 | Prass | 600/546 |
| 2004/0019370 A1 * | 1/2004 | Gliner et al. | 607/48 |
| 2004/0034340 A1 * | 2/2004 | Biscup | A61B 18/20 606/1 |
| 2004/0172114 A1 | 9/2004 | Hadzic et al. | |
| 2004/0204628 A1 * | 10/2004 | Rovegno | A61B 1/00052 600/131 |
| 2004/0260358 A1 * | 12/2004 | Vaughan | A61B 5/0488 607/48 |
| 2005/0075578 A1 * | 4/2005 | Gharib | A61B 5/0492 600/546 |
| 2005/0085743 A1 * | 4/2005 | Hacker et al. | 600/554 |

* cited by examiner

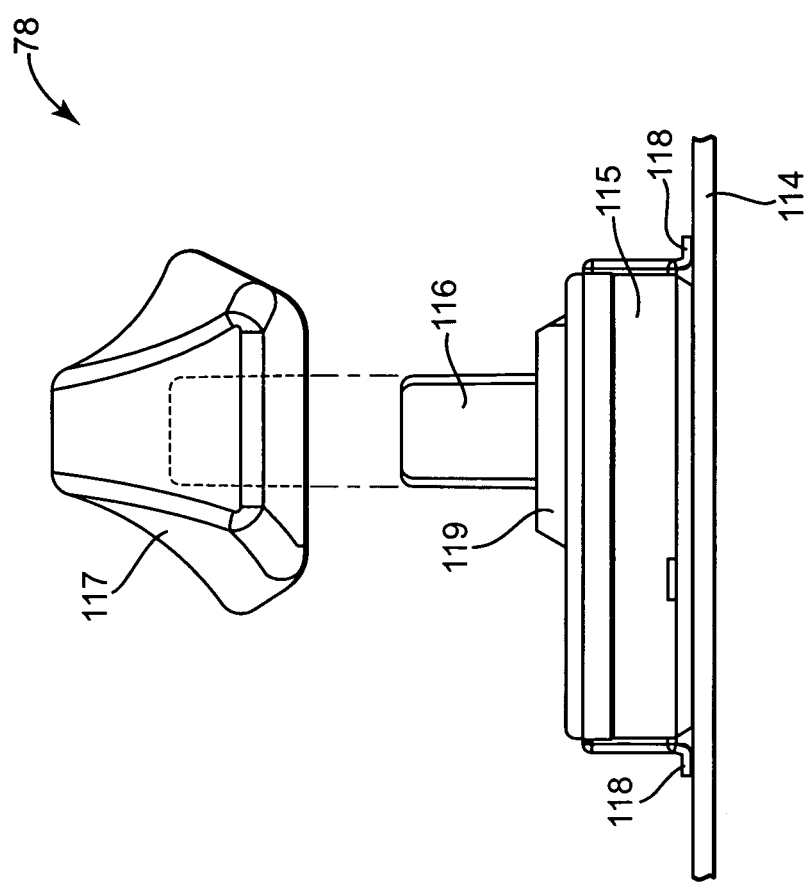

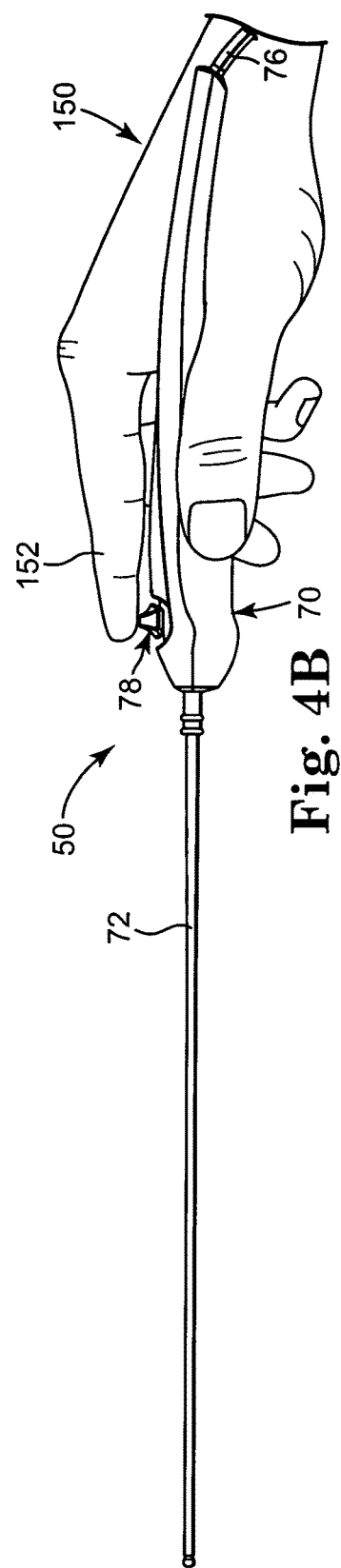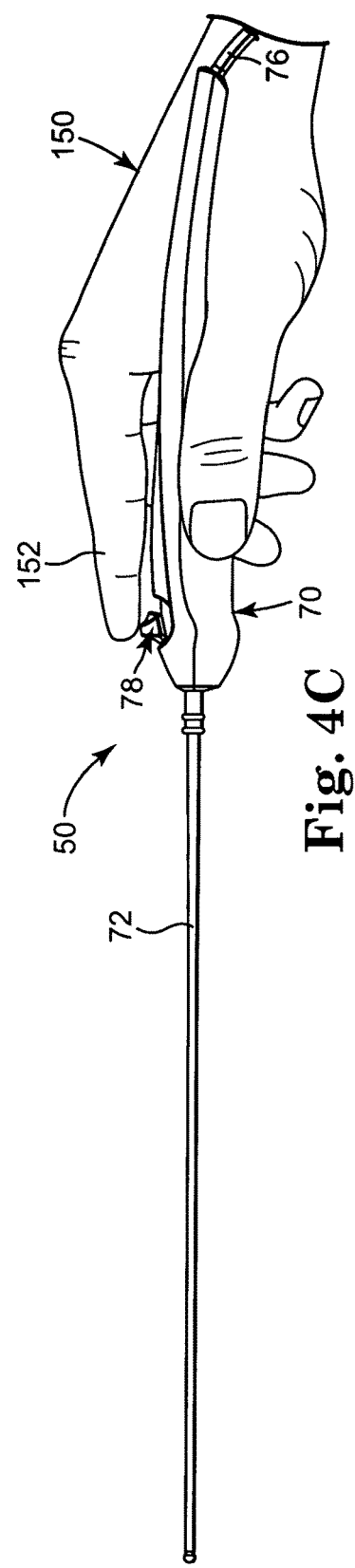

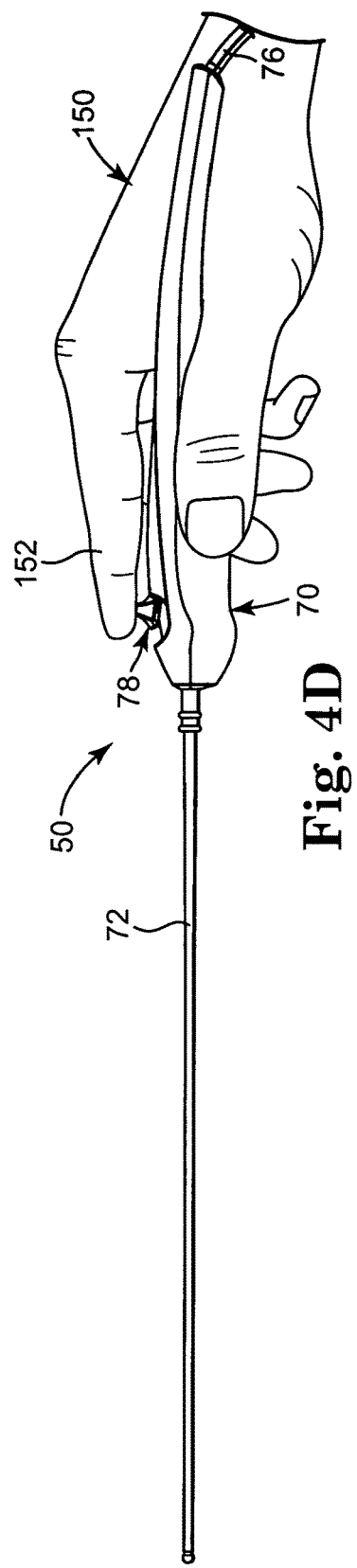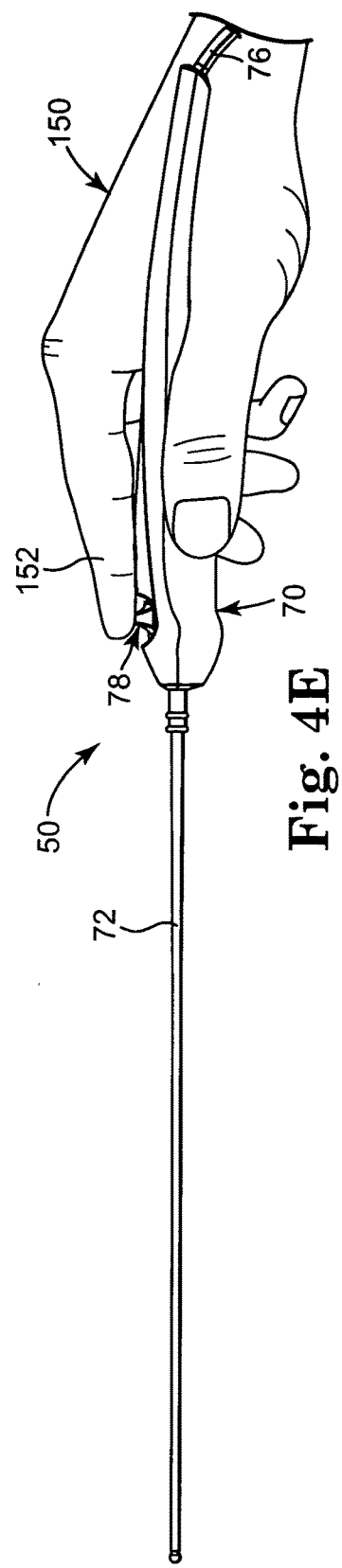

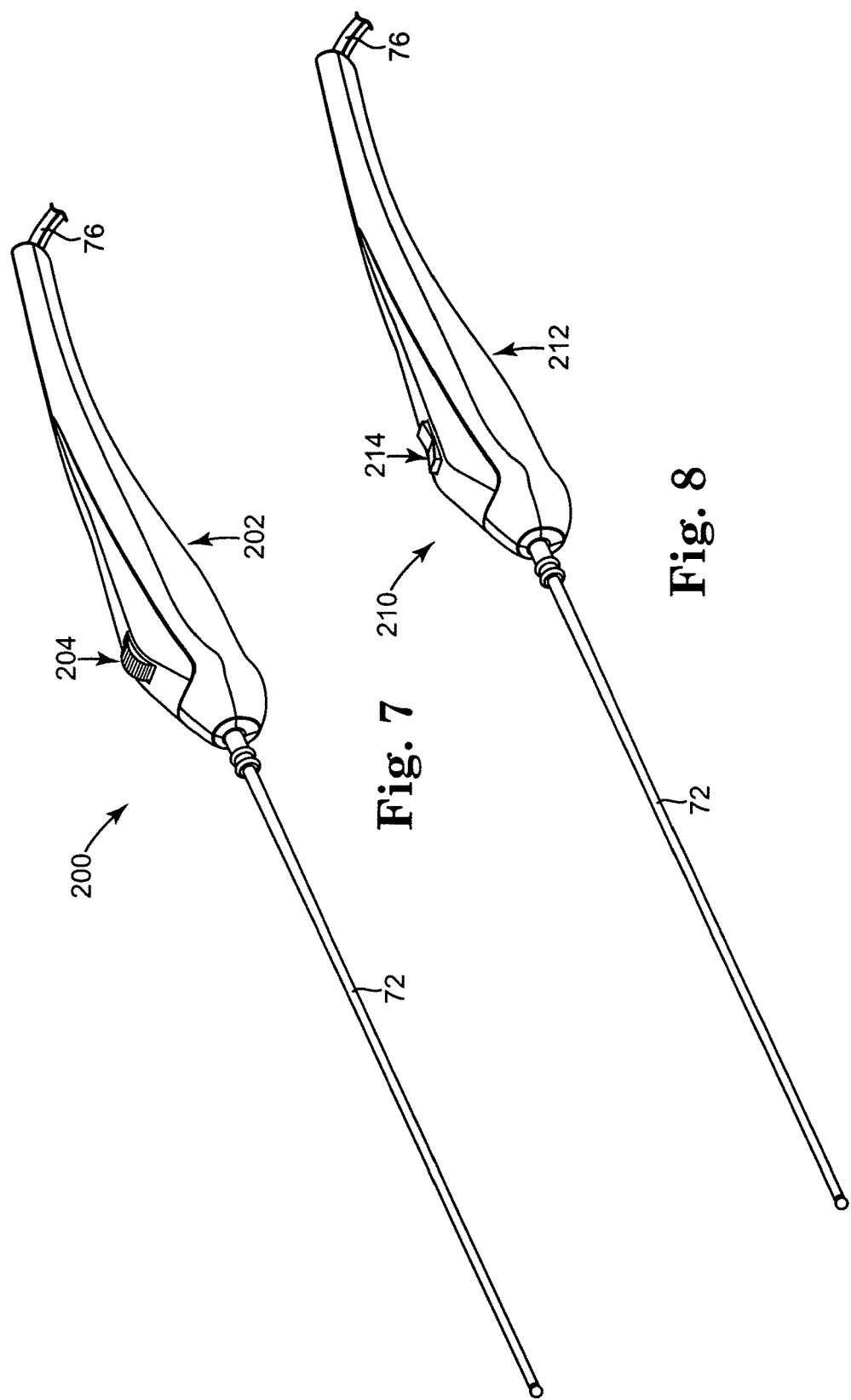

STIMULATOR HANDPIECE FOR AN EVOKED POTENTIAL MONITORING SYSTEM

BACKGROUND

The present invention relates to an evoked potential monitoring system. More particularly, it relates to a stimulator handpiece useful as part of an evoked potential monitoring system and to remotely dictate a changeable stimulation energy level delivered by a stimulus probe otherwise carried by the handpiece.

Electrophysiological monitoring assists a surgeon in locating nerves within an obscured surgical field, as well as preserving and assessing nerve function in real-time during surgery. To this end, evoked potential monitoring, such as electromyogram (EMG) monitoring, is commonly employed. In general terms, sensing or recording electrodes are coupled to appropriate tissue (e.g., cranial muscles innervated or controlled by the nerve of interest, peripheral nerve, spinal cord, brainstem, etc.). Electrical stimulation is then applied near the area where the subject nerve may be located. If the stimulation probe contacts or is reasonably near the nerve, the applied stimulation signal is transmitted through the nerve to excite the innervated tissue. Excitement of the related tissue generates an electrical impulse that is sensed by the recording electrodes (or other sensing device). The recording electrode(s) signal the sensed electrical impulse information to the surgeon for interpretation in the context of evoked potential. By way of reference, evoked potential is a relatively generic phrase that generally encompasses any system in which a stimulus is applied and a patient's response to the stimulation is recorded. EMG is but one evoked potential monitoring technique, and can provide additional information of interest to a surgeon. For example, EMG provides the reporting on individual nerve roots, whereas evoked potential monitoring, such as motor evoked potential monitoring, provides feedback on spinal cord function.

Evoked potential monitoring is useful for a multitude of different surgical procedures or evaluations that involve or relate to nerve tissue, muscle tissue, or recording of neurogenic potential. For example, various head and neck surgical procedures require locating and identifying cranial and peripheral motor nerves. Spinal surgical procedures often utilize motor evoked potential stimulation (e.g., degenerative treatments, fusion cages, etc.). While substantial efforts have been made to identify useful implementation of evoked potential monitoring, and the analysis of information generated during these monitoring procedures, certain aspects of evoked potential monitoring have remained essentially constant over time. In particular, while stimulator probes have been modified in terms of size and shape to best satisfy anatomical constraints presented by various procedures, operational capabilities of the stimulator handpiece itself continue to be fairly basic. Namely, the stimulator handpiece maintains the stimulator probe and is electrically connected to a separate control source. The surgeon manipulates the handpiece to position the probe, but can only control stimulation levels at the separate control source.

By way of example, surgery to the spine often necessitates a stabilization of the spinal column through the use of reinforcing rods and plates. The rods and plates are affixed by screws (i.e., "pedicle screws") fastened to pedicles, or bony surfaces, of selected vertebrae. To facilitate the attachment of the rods and plates, holes for the pedicle screws are bored into the selected vertebrae. The location of the pedicle holes is carefully determined to avoid impinging adjacent nerve roots. With this in mind, a surgeon creating pedicle holes has a desire to monitor the location of each pedicle hole and to ensure the integrity of the adjacent nerve root. Electrical stimulation is commonly used to evaluate the placement of a pedicle hole.

Current techniques for evaluating pedicle holes via electrical stimulation employ a handpiece maintaining a stimulation probe that is electrically coupled to a separate control source. The probe is inserted into a previously formed pedicle hole and stimulation at a first level applied thereto via operation of the separate control source. Assuming that no physical movement of the patient occurs (i.e., no nerve response), the stimulation level is incrementally increased, again by operating the separate power source until a desired, maximum stimulus level is applied with no visible patient response. Alternatively, Neubardt, U.S. Pat. No. 5,474,558, described a pedicle hole stimulator handpiece maintaining four switches that correlate to on/off, and three discrete stimulation levels. Use of the Neubartd device relies on physical movement of the patient to indicate pedicle hole mis-placement, and thus does not represent a true evoked potential monitoring system. Further, the discrete levels of stimulation control afforded by the handpiece inherently limits the stimulation level, and delivery thereof, desired by the surgeon.

The stimulator handpieces associated with other evoked potential monitoring system are similarly limited. Therefore, a need exists for an improved stimulator handpiece useful as part of an evoked potential monitoring system.

SUMMARY

One aspect of the present invention is related to an evoked potential monitoring system. The system includes a control unit and a probe assembly. The control unit can assume a variety of forms, and includes stimulator circuitry. The probe assembly includes a stimulus probe, and a stimulator handpiece selectively coupled to the stimulus probe. The handpiece includes a handle, control circuitry, and a switch. In particular, the handle defines an enclosed region. The control circuitry is disposed within the enclosed region and is electrically coupled to the stimulator circuitry. The switch is electrically coupled to the control circuitry and extends to an exterior portion of the handle. In this regard, movement of the switch remotely controls the stimulator circuitry to continuously vary a stimulation energy level delivered the stimulus probe, in one embodiment over a series of discrete, sequential steps.

Another aspect of the present invention is related to a stimulator handpiece for use with an evoked potential monitoring system. The stimulator handpiece includes a handle, a probe connector, control circuitry, and a switch. The handle defines an enclosed region. The probe connector is disposed within the enclosed region and is configured to selectively receive a stimulus probe. The control circuitry is disposed within the enclosed region and is configured to electrically communicate with a control unit. The switch is electrically coupled to the control circuitry and extends to an exterior portion of the handle, the switch having at least three degrees of freedom. In this regard, movement of the switch remotely varies an electrical signal deliverable to the control unit.

Yet another aspect of the present invention is related to a method of remotely controlling a stimulus level of an evoked potential monitoring system stimulus probe. The method includes the step of providing a probe assembly including a stimulus probe removably coupled to a stimulator handpiece. In this regard, the stimulator handpiece includes a handle defining an enclosed region, control circuitry disposed within the enclosed region and electrically coupled to stimulator circuitry disposed in a remote control unit, and a switch electrically coupled to the control circuitry and extending to an exterior portion of the handle. The method additionally includes the step of contacting the stimulus probe with an anatomical body part. The method further includes the step of moving the switch to vary a stimulation energy level delivered by the stimulus probe over a series of discrete, incremental steps. Further, a physiological response of the patient to the stimulation energy is electronically recorded.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

FIG. 3A is an exploded view of a portion of the probe assembly of FIG. 2, including a switch coupled to a printed circuit board according to one embodiment of the present invention;

FIGS. 4B-4E are side views of the probe assembly of FIG. 2 illustrating selected movement of a switch through at least one degree of freedom according to embodiments of the present invention;

FIG. 7 is a perspective view of an alternate embodiment probe assembly employing a rotating wheel switch in accordance with the present invention; and FIG. 8 is a perspective view of another alternate embodiment probe assembly employing a rocker arm switch in accordance with the present invention.

DETAILED DESCRIPTION

Figure 1:
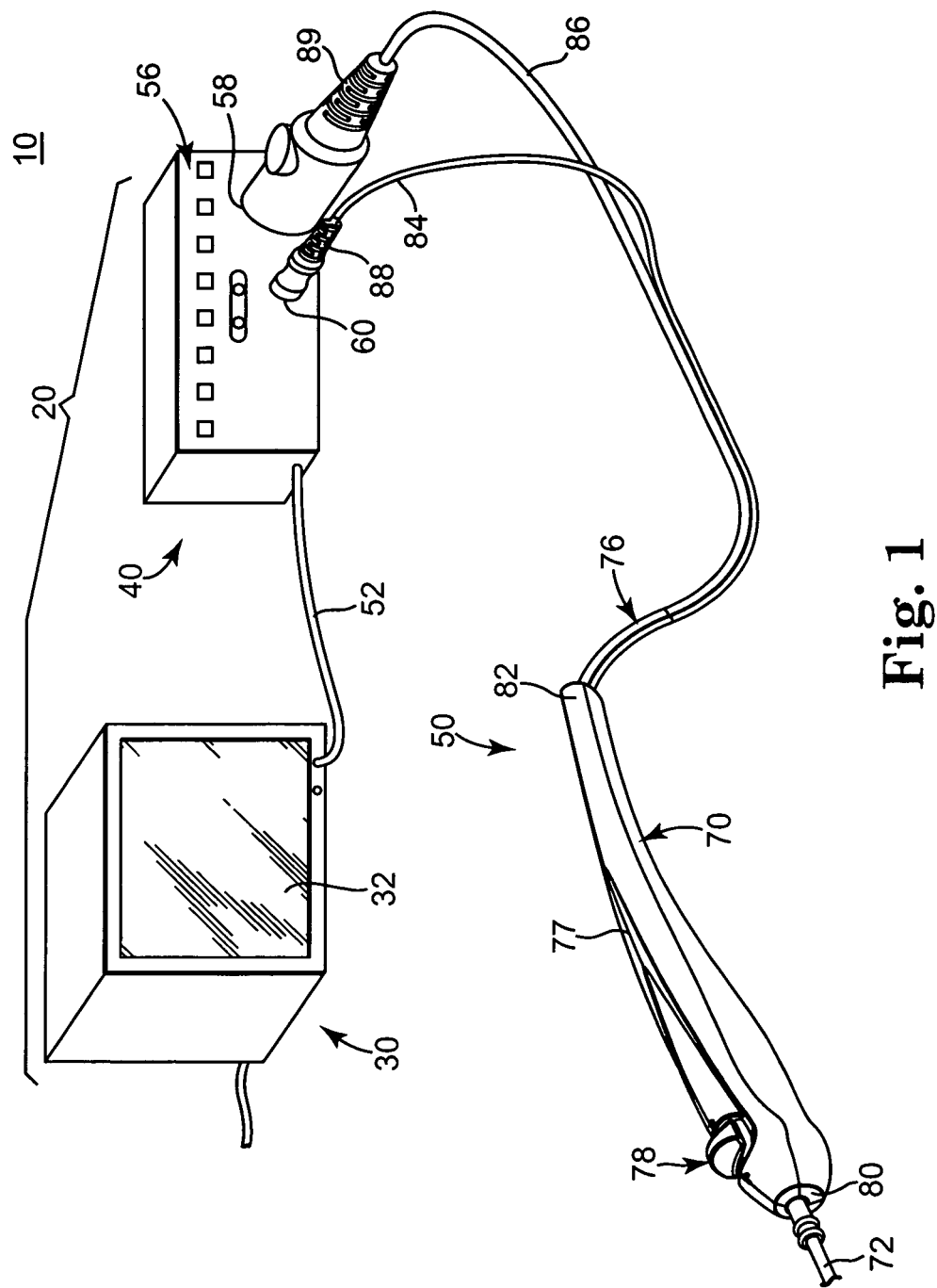
FIG. 1 is a perspective view of an evoked potential monitoring system illustrating a probe assembly according to one embodiment of the present invention.

An evoked potential monitoring system 10 according to one embodiment of the present invention is illustrated in FIG. 1. In general terms, the system 10 is configured to assist in and perform evoked potential monitoring for virtually any nerve/muscle combination of the human anatomy, as well as recording nerve potential. The system 10 includes a control unit 20 and a probe assembly 50. As described in greater detail below, the control unit 20 can assume a wide variety of forms and in one embodiment includes a console 30, having a monitor 32, and a patient interface module 40. Regardless, the control unit 20 facilitates operation of the probe assembly 50, as well as processes all information generated by other system 10 components (not shown) during use. More particularly, the probe assembly 50 and the control unit 20 are adapted to allow control and variation of a stimulus energy delivered to, and thus an stimulus level delivered by, the probe assembly 50 via an actuator provided on the probe assembly 50 (remote of the control unit 20). To this end, the probe assembly 50 and the control unit 20 are adapted to allow continuous variation (e.g., increment or decrement) of the stimulation energy over a series of discrete, sequential steps via manipulation of the probe assembly 50 actuator. Further, when performing an evoked potential monitoring procedure, the control unit 20 processes information (e.g., patient response) resulting from delivered stimulation. For example, the system 10 can include one or more sensing devices (not shown), such as sensing or recording electrodes, that are employed to sense or measure a patient's response (if any) to stimulation applied by the probe assembly 50. From these processed results, an evoked potential evaluation can be performed.

In one embodiment, the system 10 performs monitoring based upon recorded EMG activity in response to an electrical current energy delivered by the probe assembly 50. Alternatively, the system 10 can be adapted to employ other evoked potential monitoring techniques (e.g., directly sensing nerve response to stimulation energy applied by the probe assembly 50, etc.). Regardless, with the one embodiment of FIG. 1, the console 30 and the patient interface module 40 are provided as separate components, communicatively coupled by a cable 52. Alternatively, a wireless link can be employed. Further, the console 30 and the patient interface module 40 can be provided as a single device. In basic terms, however, the patient interface module 40 serves to promote easy connection of stimulus/sensory components (such as the probe assembly 50), as well as to manage incoming and outgoing electrical signals. The console 30, in turn, interprets incoming signals (e.g., impulses sensed by sensing or recording electrodes), displays information desired by a user, provides a user interface (such as by including, for example, a touch screen), and delivers a stimulation energy to the probe assembly 50 pursuant to control signals from the probe assembly 50 (via connection to the patient interface module 40), as well as other tasks as desired. The stimulation energy can be continuously increased or decreased over a series of discrete, sequential steps.

With the above general operational parameters in mind, the console 30 is configured to facilitate evoked potential monitoring with at least one, preferably at least four, channels of EMG monitoring. In one embodiment, the console 30 is an alternating current (AC) powered console; alternatively, the console 30 can be battery powered. To this end, the console 30 is capable of delivering a stimulation current or voltage to the probe assembly 50 via the patient interface module 40, and in particular at varying levels based upon control signals initiated by a user of the probe assembly 50. For example, the console 30 is preferably adapted to generate a multiplicity of discrete stimulation energy levels over a range of 0-30 mA in increments of 0.01, 0.05, 1.0, or 5.0 mA. The sensitivity of the incremental adjustments (i.e., increase or decrease in stimulation energy level) can be selected by the user or can be a single, pre-determined value (e.g., the console 30 can be adapted to facilitate variation in the delivered stimulation energy level in increments of 1.0 mA only). Even further, the console 30 can be adapted to continuously increase or decrease the stimulation energy level (in response to signals from the probe assembly 50) in a non-linear fashion. For example, the console 30 can be adapted to increase or decrease the delivered stimulation in increments of 0.01 mA for a first time period followed by 1.0 mA incremental changes for subsequent, second time period immediately following the first time period. In one embodiment, the console 30 is further connected to, and controls operation of, auxiliary items such as a printer (not shown) other stimulus probes, etc., in response to control signals from the probe assembly 50 (as well as by direct operation of the console 30 in one embodiment). The processing of probe assembly control signals by the console 30 is described below.

As previously described, the patient interface module 40 communicates with the console 30 through the cable 52 information to and from the probe assembly 50, as well as information from other sensing components (not shown), such as sensing or recording electrodes. In effect, the patient interface module 40 serves to connect the patient (not shown) to the console 30. To this end, and in one embodiment, the patient interface module 40 includes one or more (preferably eight) sensory inputs 56, such as pairs of electrode inputs (illustrated schematically in FIG. 1). In addition, the patient interface module 40 provides a simulator input port 58 (referenced generally in FIG. 1) and a stimulator output port 60 (referenced generally in FIG. 1). As described below, the stimulator input port 58 receives control signals from the probe assembly 50 relating to desired stimulation levels and/or other activities, whereas the stimulator output port 60 facilitates delivery of stimulation energy to the probe assembly 50. The patient interface module 40 can further provide additional component port(s), such as a ground (or return electrode) jack, auxiliary ports for additional stimulator probe assemblies, etc. Conversely, one or more of the ports 56-60 can be eliminated (such as where the probe assembly 50 is directly connected to the console 30).

The control unit 20, and in particular the console 30 and the patient interface module 40, are akin in several respects to available monitoring systems, such as the NIM-Response™ Nerve Integrity Monitor, available from Medtronic Xomed of Jacksonville, Fla. For example, the touch screen capabilities provided by the NIM-Response™ Nerve Integrity Monitor can be incorporated into the control unit 20 of the present invention. In addition, however, the system 10 of the present invention, and in particular the probe assembly 50 in combination with appropriate stimulation circuitry associated with the console 30 and/or the patient interface module 40, affords the surgeon control of the stimulation energy delivered by the probe assembly 50 on a continuous basis over a series of discrete, incremental or sequential steps via manipulation of an actuator provided on the probe assembly 50 itself as part of an evoked potential monitoring operation, features not otherwise provided by available monitoring systems or stimulator handpieces. Thus, the control unit 20 can vary significantly from the one embodiment described while remaining within the scope of the present invention.

The probe assembly 50 is, in one embodiment, a monopolar stimulation device and includes a stimulator handpiece 70, a stimulus probe 72 selectively coupled to the handpiece 70, cabling 76 extending from the surgical handpiece 70 and attachable to the patient interface module 40, and control circuitry (not shown in FIG. 1). The stimulator handpiece 70 includes a handle 77 maintaining a switch 78.

More specifically, the handle 77 defines a probe end 80 and a cable end 82. The cabling 76 extends from the cable end 82 to the patient interface module 40. Alternatively, the cabling 76 can be coupled to the console 30. In a preferred embodiment, the cabling 76 is a dual section cable including an energy supply cable 84 and a control cable 86. A first strain relief harness 88 is provided to reinforce the energy supply cable 84, and a second strain relief harness 89 is provided to reinforce the control cable 86. As a point of reference, the energy supply cable 84 is configured to couple with the stimulator output port 60 and the control cable 86 is configured to couple with the stimulator input port 58 of the patient interface module 40.

Figure 2:
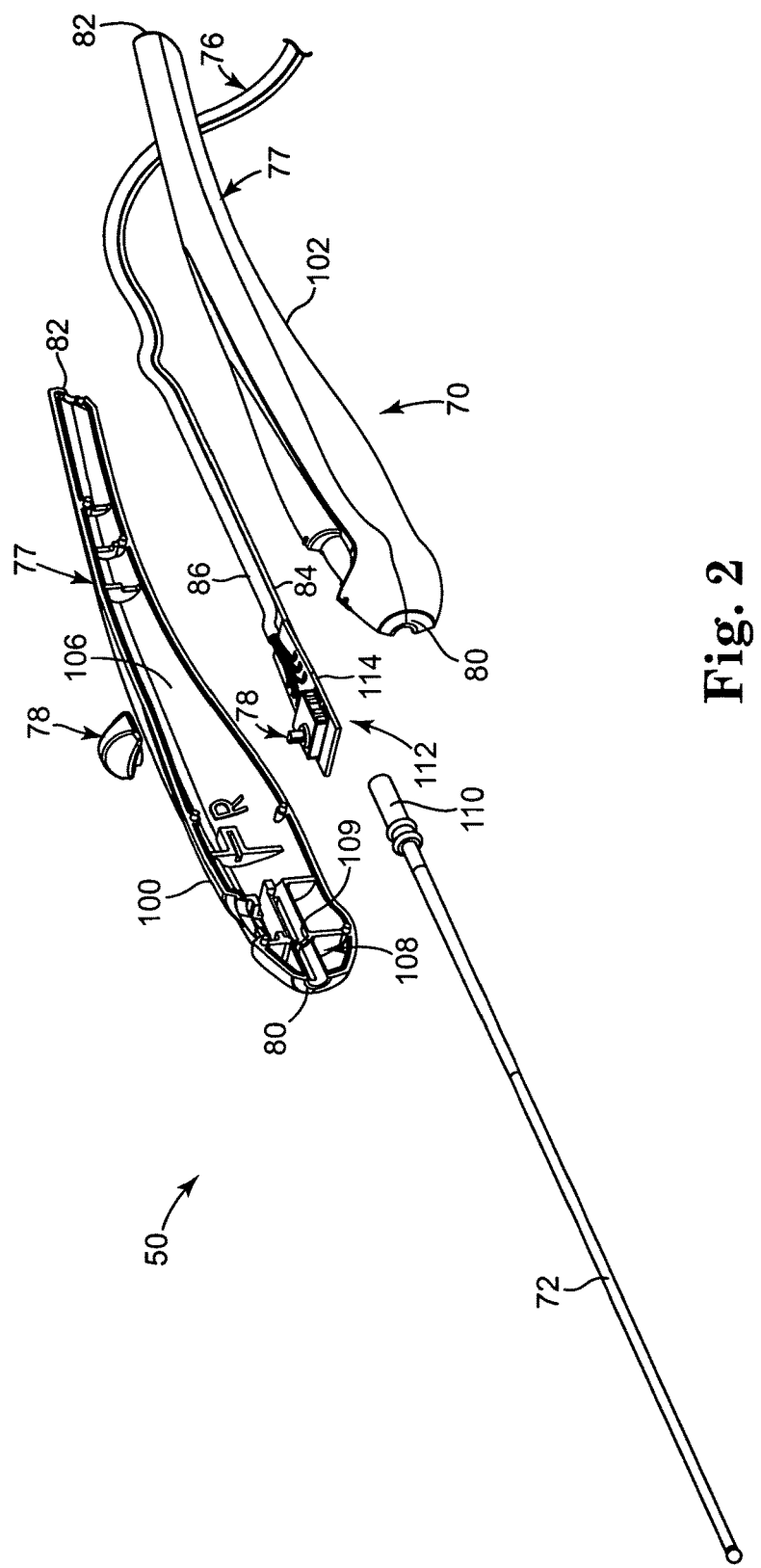
FIG. 2 is an exploded view of a probe assembly component of the system of FIG. 1.

FIG. 2 is an exploded view of the probe assembly 50 according to one embodiment of the present invention. In particular, in the view of FIG. 2, the stimulation handpiece 70 has been disassembled to describe the orientation and relationship of the various components. In this regard, the handle 77 includes a first section 100 and a second section 102 each configured for mating attachment to the other. When assembled, the first and second sections 100, 102 collectively form the probe end 80, the cable end 82, and an enclosed region 106.

In one embodiment, the handle sections 100, 102 are formed of a durable engineering plastic suited for repeated cleaning and/or sterilization. Exemplary engineering plastics for forming the handle 77 include high-density polyethylene, acrylonitrile butadiene styrene (ABS), nylon in general, and polyester in general. In an alternate embodiment, the handle 77 is formed of a durable and rust resistant metal, for example stainless steel. Even further, the handle 77 can be integrally formed as a homogenous body.

A probe connector 108 is formed by the handle sections 100, 102 within the enclosed region 106 adjacent to the probe end 80 and is configured to selectively receive the stimulus probe 72. As a point of reference, corresponding portions of the probe connector 108 are, in one embodiment, formed by each of the handle section 100, 102, although only the portion associated with the section 100 is visible in the view of FIG. 2. The probe connector 108 is preferably a quick release probe connector such that the stimulus probe 72 can easily be disposed of following use and/or replaced with a differently configured stimulus probe 72. Alternatively, a more permanent assembly between the probe connector 108 and the stimulus probe 72 can be provided. In one embodiment, the probe connector 108 includes an engagement surface 109 suited for engaging an engagement shaft 110 of the stimulus probe 72. Further, the energy supply cable 84 terminates in a connector (not shown), such as a Molex connector, adapted to electrically couple the energy supply cable 84 to the stimulus probe 72 upon final assembly. Regardless, the stimulus probe 72 can be any one of a variety of tissue, bone, and/or nerve stimulator probes. Therefore, while the stimulus probe 72 is depicted as a ball point nerve probe, it is to be understood that other shapes and sizes of probes useful for supplying stimulation energy to muscle, tissue, and/or nerves are equally appropriate for use with the surgical handpiece 70. For example, the stimulus probe 72 can alternatively be a Prass flush tip probe, Kartush stimulus dissector (KSC Instruments), a Yingling flex tip probe, a modified stimulation probe, etc. Even further, the probe assembly 50, including the stimulus probe 72, can be configured as a bipolar stimulation device.

As shown in FIG. 1, control circuitry 112 including a printed circuit board 114 is disposed within the enclosed region 106 and is electrically coupled to the control cable 86 (that, in one embodiment, includes a bundle of six wires). As described above, the cabling 76 is preferably a dual section cable including the energy supply cable 84 and the control cable 86. With this in mind, when the stimulator handpiece 70 is assembled, the energy supply cable 84 electrically communicates with the stimulus probe 72, and the control cable 86 bifurcates from the energy supply cable 84 to electrically couple with the printed circuit board 114. In this manner, the control circuitry 112 within the enclosed region 106 is physically separated from the stimulator circuitry (not shown) within the control unit 20 (FIG. 1).

The printed circuit board 114 is electrically connected to the control cable 86 and controls electrical signals sent from the switch 78 to the stimulator circuitry (not shown) housed in the control unit 20 (FIG. 1). In particular, the printed circuit board 114 is electrically coupled to the switch 78 such that the control circuitry 112 prompts delivery of stimulation energy to the stimulus probe 72 in response to movements of the switch 78, as described below. Notably, while the control circuitry 112 is operatively coupled to the control unit 20, the control circuit 112 is electrically isolated from the patient and the surgeon during use.

FIG. 3A is an exploded view of the switch 78 connected to the printed circuit board 114. In one embodiment, the switch 78 is a multi-directional, momentary action switch and includes an actuator 115, a post 116 and a pad 117. The actuator 115 is electrically connected to the printed circuit board 114 via terminals 118. In one embodiment, the terminals 118 are gullwing terminals suitable for being soldered to the printed circuit board 114. The post 116 is pivotally mounted to the actuator 115 via a sealed joint 119. In one embodiment, the sealed joint 119 is a polymeric sealed joint permitting the post 116 to gyrate in relation to the actuator 115. The pad 117 slidably fits over the post 116 and is ergonomically shaped to permit deft manipulation of the switch 78. Switches suitable for implementing embodiments of the present invention include TPA Series Navigation Tact Switches available from, for example, ITT Industries, Inc., White Plains, N.Y.

With additional reference to FIG. 2, when the stimulator handpiece 70 is assembled, the switch 78 is assembled to the handle 77 such that the post 116 extends from the enclosed region 106 to an exterior portion of the handle 77 where the post 116 is capped by the pad 117. The handle 77 and the pad 117 combine to seal the surgical handpiece 70 against entrance of liquids possibly encountered during a surgical procedure. Manipulation of the pad 117 moves the post 116 relative to the actuator 115. The actuator 115 translates movement of the post 116 into an electrical signal that is communicated through the control cable 86 to the control unit 20 (FIG. 1). The stimulator circuitry (not shown) within the control unit 20 interprets the electrical signal and responds with an electrical command that is transferred through the energy supply cable 84 to the stimulus probe 72 and/or to other components (e.g., a printer, additional stimulator probe, other surgical device, etc.). In this manner, movement of the switch 78 at the surgical handpiece 70 triggers a remote response from the stimulator circuitry in the control unit 20.

Figure 3B:
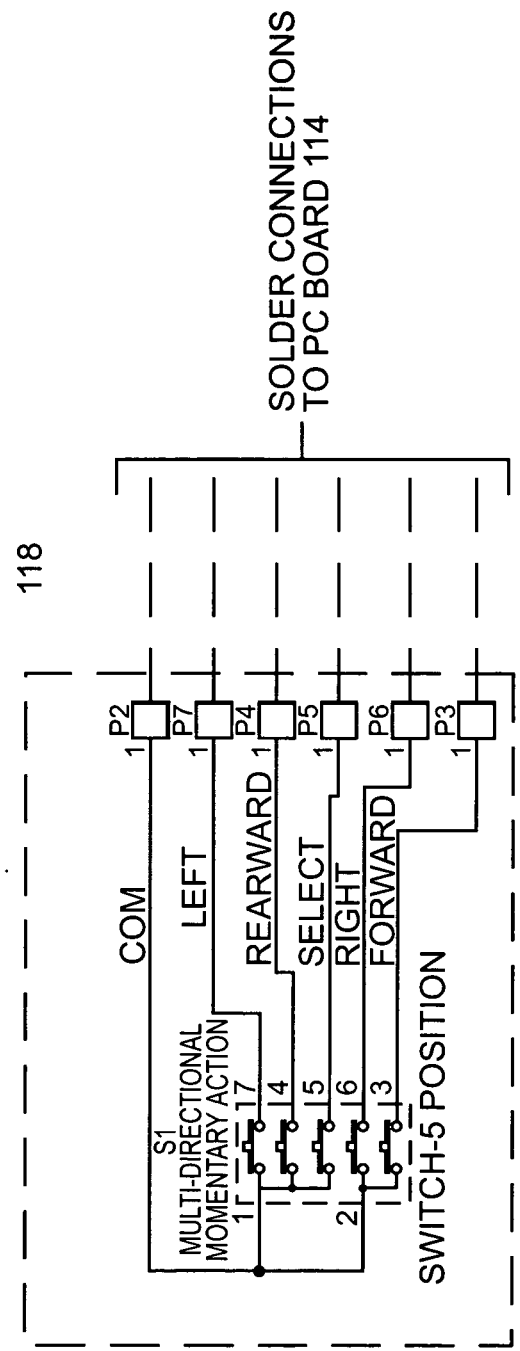
FIG. 3B is a simplified electrical diagram of a portion of the probe assembly of FIG. 2 in accordance with the present invention, illustrating connection of the switch to the printed circuit board.

In one embodiment, the switch 78 can assume (i.e., move or pivot between) at least a forward position, a rearward position, and a neutral position, and can be depressed downward when in any one of the forward, rearward, or neutral positions. Even further, the switch 78 is operable between left and right positions (relative to the neutral position). Once again, "movement" of the switch 78 is characterized as the post 116 moving relative to the actuator 115 via manipulation of the pad 117. The simplified wiring diagram of FIG. 3B illustrates one possible electrical connection of the actuator 115 to the printed circuit board 114, including an indication of possible terminal 118 designations or commands.

Figure 4A:
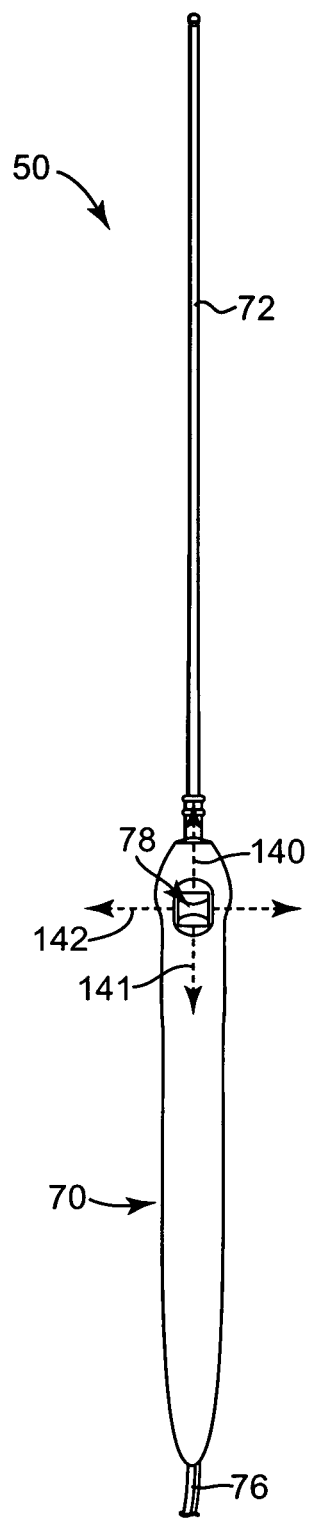
FIG. 4A is a top view of the probe assembly of FIG. 2 illustrating degrees of freedom of a switch in accordance with the present invention.

In a preferred embodiment, the switch 78 gyrates through a range of positions, as described below. For example, FIG. 4A is a top view of the probe assembly 50 illustrating the switch 78 in a neutral position. FIG. 4A further illustrates that the switch 78 can be moved longitudinally to occupy a forward distal position 140 and, alternately, a rearward proximal position 141 (movement to the positions is indicated by arrows 140 and 141, respectively). In this regard, the longitudinal movement of the switch 78 to the distal forward 140 and the proximal rearward 141 positions entails two degrees of freedom referred to as a pitch movement. In one embodiment, the switch 78 can pitch from the neutral position a distance of approximately 0.5 mm to the distal forward 140 position and a can pitch a similar distance of approximately 0.5 mm to the proximal rearward 141 position, although the probe assembly 50 can be configured to provide other pitch dimensions.

In addition, the switch 78 can be moved laterally as indicated by arrow 142. The lateral movement of the switch 78 indicated by the arrow 142 entails two degrees of freedom (i.e., left and right in the orientation of FIG. 4A) referred to as a roll movement. In one embodiment, the switch 78 can roll laterally from the neutral position a distance of approximately 0.5 mm in each of the lateral (i.e., left and right) directions as indicated by the arrow 142, although the probe assembly 50 can be configured to provide other roll dimensions.

Moreover, the switch 78 moves flexibly via the sealed joint 119 (FIG. 3) and can be depressed downward (i.e., directed into the paper) and can rebound upward, and entails two degrees of freedom (i.e., downward and upward) referred to as an axial movement. In one embodiment, the switch 78 can move axially when in any of the forward, rearward, or lateral positions. In view of the above, in one embodiment, the switch 78 is movable through a range of motions defined by six degrees of freedom.

FIGS. 4B-4E are each a side view of the probe assembly 50 shown in FIG. 1 during use. The side view of FIG. 4B illustrates a hand 150 of a surgeon holding the surgical handpiece 70 such that a finger, for example an index finger 152, is positioned to manipulate the switch 78 and in particular the pad 117. As illustrated in FIG. 4B, the switch 78 is in the neutral position and the index finger 152 is posed for selective manipulation of the switch 78 at the discretion of the surgeon. In this regard, during use when the switch 78 in the neutral position, the system 10 (FIG. 1) is adapted to maintain a current stimulation energy (or stimulus level) setting delivered to, and thus by, the stimulus probe 72 (i.e., a static stimulus level, for example a stimulus level previously selected by the surgeon upon initiation of the system 10). The static stimulus level can be any stimulation energy level available with the system 10, including no stimulation energy, and movement of the switch 78 varies the stimulus level delivered to the stimulus probe 72 from the static stimulus level.

FIG. 4C is a side view the probe assembly 50 showing the switch 78 pitched distally to a forward position. In this regard, the index finger 152 is shown displacing the switch 78 toward the stimulus probe 72. In one embodiment, displacement of the switch 78 to the forward position causes the actuator 115 (FIG. 3A) to signal the control circuitry 112 (FIG. 2) to send a signal to the stimulator circuitry in the control unit 20 (FIG. 1), triggering or prompting an increment (i.e., an increase) in the electrical current, and thus the stimulus level, delivered to the stimulus probe 72. In one embodiment, the system 10 (FIG. 1) is adapted such that when the switch 78 is retained (i.e., held) in the forward position, the stimulus level delivered to the stimulus probe 72 is continuously increased over a series of discrete, incremental steps. As described below, in one embodiment, the system 10 (FIG. 1) is adapted such that where the switch 78 is held in the forward position for an extended period of time, the rate at which the delivered stimulus level increases occurs more rapidly (e.g., the incremental steps in stimulus level become larger).

FIG. 4D is a side view of the probe assembly 50 showing the switch 78 pitched proximally to a rearward position. In one embodiment, displacement of the switch 78 to the rearward position causes the actuator 115 (FIG. 3) to signal the control circuitry 112 (FIG. 2) to send a signal to the stimulator circuitry in the control unit 20 (FIG. 1), triggering or prompting a continuous decrement (i.e., decrease) in the electrical current, and thus the stimulation energy, delivered to the stimulus probe 72. When the switch 78 is retained (i.e., held) in the rearward position, the system 10 (FIG. 1) is adapted such that the stimulation energy delivered to, and thus by, the stimulus probe 72 is continuously decremented over a series of discrete, incremental steps.

FIG. 4E is a side view of the probe assembly 50 illustrating the switch 78 in a depressed position. In particular, the index finger 152 of the surgeon is depressing the switch 78 axially to the depressed position. In one embodiment, the system 10 (FIG. 1) is adapted such that pressing the switch 78 downward signals or prompts the control unit 20 to operate an auxiliary item. For example, pressing the switch 78 downward can prompt the control unit 20 to generate a printout of information displayed on the monitor 32 (FIG. 1), such as by controlling operation of a separate printer (not shown). In this manner, information of interest to the surgeon (e.g., current stimulation settings, evoked potential readings, EMG activity readings, etc.) can be captured for archival purposes during any instant of the surgical procedure. Alternatively, a wide variety of other operations can be prompted by pressing of the switch, such as saving information to a disk, initiate a monitoring sequence of another piece of equipment otherwise connected to the control unit 20 (e.g., SSEP monitoring), control stimulus level of a separate probe, etc.). In addition, in one embodiment, pressing the switch 78 downward and holding for an extended period of time (e.g., at least one second) is interpreted by the control unit 20 as a request to terminate the delivery of stimulation energy to the stimulus probe 72, resulting in a stimulus level of zero mA. As a point of reference, the switch 78 can be depressed downward when the switch 78 is in any one of the forward, neutral, or rearward positions such that the surgeon can selectively print the information displayed on the monitor 32 or terminate electrical stimulation at any point in the procedure.

With the above descriptions of the switch 78 in mind, the probe assembly 50 is operable by the surgeon to apply the desired stimulus level to an anatomical feature, continuously increment or decrement the stimulus level over a series of discrete, incremental steps, terminate the stimulus or maintain the desired stimulation current, prompt operation of an auxiliary device (e.g., print the associated display screen data from the monitor 32), and/or zero the stimulus level of the stimulus probe 72 during intraoperative evoked potential monitoring events. Alternately, other actions can be facilitated and/or one or more of the features described above can be eliminated. For example, the system 10 (FIG. 1) can be adapted such that roll movements of the switch 78 prompt other activities/operational features via the control unit and/or other system components (e.g., changing or toggling between display screens on the monitor 32, altering operational parameters (e.g., probe or electrode sensitivity), etc.). Even further, the probe assembly 50 can include one or more additional switches (not shown), that may or may not be identical to the switch 78, on the handpiece 70 that facilitate one or more of the auxiliary actions described above (or any other feature associated with the control unit 20 (FIG. 1)).

In one embodiment, the switch 78 is a joystick movable through at least three degrees of freedom, preferably through six degrees of freedom, as described above. In particular, the switch 78 can be translated and/or rotated and/or depressed across a full range of pitch, roll, and axial movements such that the switch 78 is not limited to linear movements. In this manner, movement of the switch 78 enables the surgeon otherwise handling the probe assembly 50 during an evoked potential monitoring procedure to remotely and continuously control the stimulus level delivered to the stimulus probe 72 over a series of discrete, incremental steps.

In one embodiment, the system 10 is programmed to have a default stimulation frequency of 5 Hz, a pulse duration of 100 microseconds, and a stimulus current level that is adjustable via the switch 78 from 0-30 mA in increments of 0.05, 0.01, 1.0, or 5.0 mA. In one embodiment, the probe assembly 50 is a monopolar stimulation probe configured such that the electrical current is delivered through the stimulus probe 72 and returns to a ground electrode (not shown) attached to the patient. In an alternate embodiment, the probe assembly 50 is a bipolar probe suited for general use as a nerve locator. In any regard, the probe assembly 50 has a frequency range of 1-10 Hz, preferably the frequency is delivered at 5 Hz, and a pulse duration in the range of 50-250 microseconds adjustable in 50 microsecond increments, and a stimulus current level adjustable in the range of 0-30 mA via manipulation of the switch 78 through one of at least three degrees of freedom.

Figure 5:
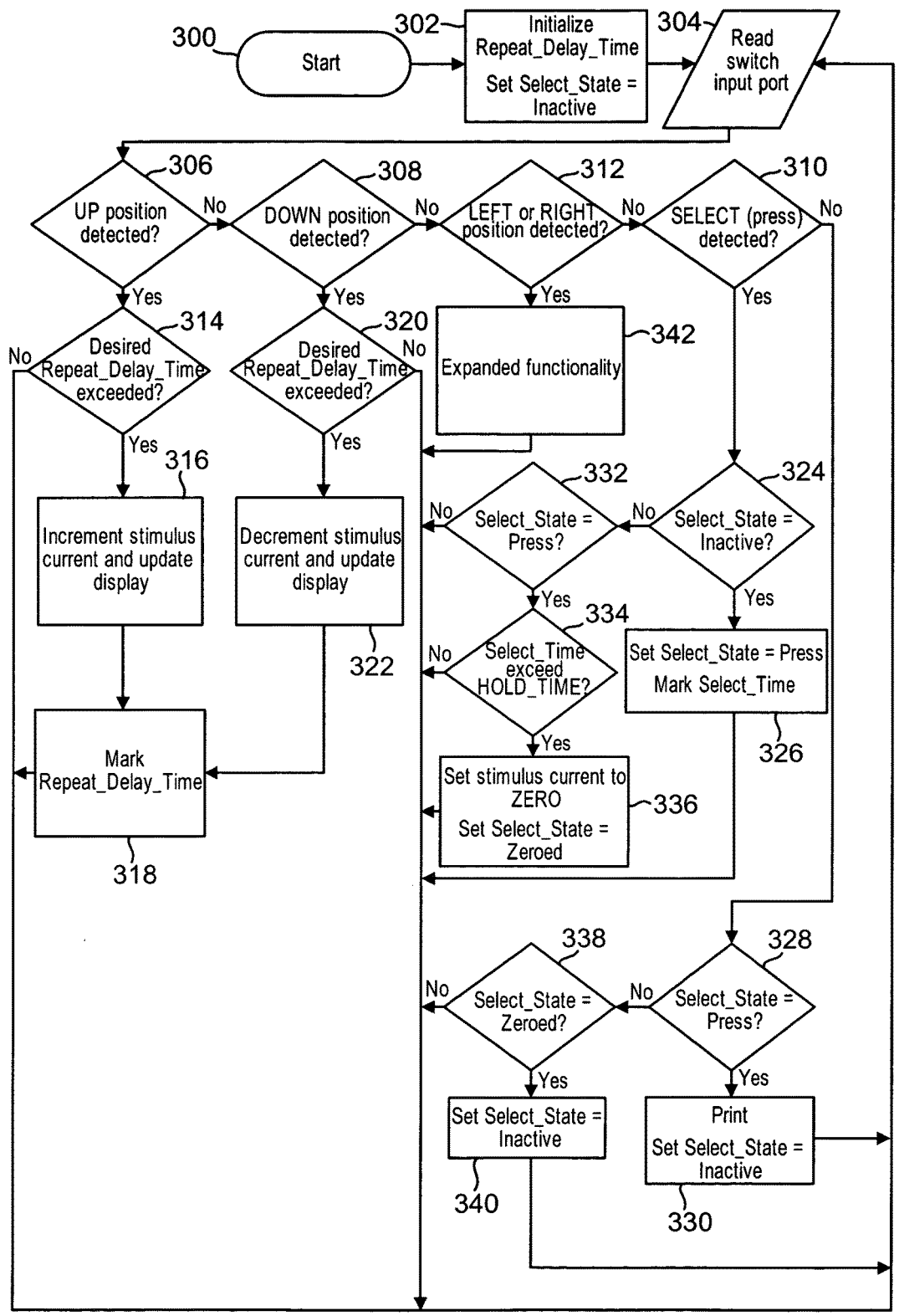
FIG. 5 is a block diagram illustrating operation of a control unit in response to signals from the probe assembly of FIG. 2.

As previously described, the control unit 20 (FIG. 1), for example the console 30 and/or the patient interface module 40, includes stimulator circuitry and related software/hardware for receiving, interpreting, and acting in response to signals from the probe assembly 50, and in particular signals generated by manipulation of the switch 78. With this in mind, FIG. 5 is a simplified block diagram illustrating operation of the stimulation circuitry/programming in accordance with one embodiment of the present invention. At step 300, the system 10 (FIG. 1) is activated, followed by initialization of the stimulation circuitry control parameters at step 302. In particular, the stimulation programming initializes a "Repeat_Delay_Time" value that otherwise designates the length of time the switch 78 (FIG. 2) must remain in a particular position (e.g., pitched forward or rearward, rolled left or right, etc.) before an action is taken by the control unit 20. The Repeat_Delay_Time value can be a default number (e.g., 0.5 second) or can be designated by the user. Further, the stimulation programming initially designates that a state of the switch is "inactive" (i.e., "Select_State"); as described below, the "state" can be "press" (interpreted as a request to generate a screen print out), "zeroed" (interpreted as a request to cease the deliver of stimulation energy), or "inactive" (interpreted as being status quo, whereby stimulation energy is delivered to the probe assembly 50 and no screen print outs are being generated).

At step 304, a signal from the probe assembly 50 (FIG. 1) is read. In particular, any signal generated by the switch 78 (FIG. 2) is transferred via the control cable 86 (FIG. 2) to the stimulation circuitry/programming, such as via the patient interface module 40 (FIG. 1). Once again, the switch 78 is remote of the control unit 20 (FIG. 1), and is manipulated in a desired fashion by the surgeon. Regardless, the read switch signal is interpreted at steps 306-312.

For example, at step 306, a determination is made as to whether the read switch signal is indicative of the switch 78 (FIG. 2) being in the pitched forward position of FIG. 4C (designated as "UP position") in FIG. 5. If "yes", at step 314 the length of time the switch 78 has been in the pitched forward position is compared to the "Repeat_Delay_Time" value. If the time period the switch 78 has been in the pitched forward position is less than the Repeat_Delay_Time value ("no" at step 314), the stimulator programming returns to step 304 and continues to read the switch signal. Conversely, if the switch 78 has been in the pitched forward position for a time period greater than the Repeat_Delay_Time value ("yes" at step 314), the control unit 20 operates to incrementally increase the stimulation energy delivered to the probe assembly 50, and in particular the stimulus probe 72 (FIG. 2), at step 316 over the series of discrete, sequential energy level steps available with the control unit 20. Further, the display provided to the surgeon via the control unit 20 is updated to reflect the increased stimulation energy level. Subsequently, at step 318, the "Repeat_Delay_Time" value is "marked" or held until the switch signal (at step 304) is identified as being something other than the pitched forward position; under these circumstances, then, the stimulation energy level will continue to increase over the discrete, incremental series of energy level steps until a switch signal other than "pitched forward" is sensed. In one embodiment, "marking" of the Repeat_Delay_Time value facilitates a non-linear increase in the delivered stimulation energy level over time. For example, for the stimulator circuitry/programming can be adapted such that for the first two seconds the switch 78 is in the pitched forward position, the energy level increases in increments of 0.01 mA; for the next five seconds the switch 78 is in the pitched forward position, the energy level increases in increments of 0.05 mA; in increments of 1.0 mA for the next five seconds; and increments of 5.0 mA thereafter. Once the switch 78 is release from the pitched forward position, the rate of increase returns to the smallest incremental change value. Alternatively, the energy level can increase in incremental steps linearly over time with the switch 78 in the forward position.

Step 308 relates to the switch signal reflecting the switch 78 (FIG. 2) being maneuvered to the pitched rearward position of FIG. 4D (designated as "DOWN position" in FIG. 5). In particular, a determination is made as to whether the read switch signal is indicative of the switch 78 being in the pitched forward position. If "yes", at step 320 the length of time the switch 78 has been in the pitched rearward position is compared to the "Repeat_Delay_Time" value. If the time period the switch 78 has been in the pitched rearward position is less than the Repeat_Delay_Time value ("no" at step 320), the stimulator programming returns to step 304 and continues to read the switch signal. Conversely, if the switch 78 has been in the pitched rearward position for a time period greater than the Repeat_Delay_Time value ("yes" at step 320), the control unit 20 operates to incrementally decrease the stimulation energy delivered to the probe assembly 50, and in particular the stimulus probe 72 (FIG. 2), at step 322. Further, the display provided to the surgeon via the control unit 20 is updated to reflect the decreased stimulation energy level. Subsequently, at step 318, the "Repeat_Delay_Time" value is "marked" or held until the switch signal (at step 304) is identified as being something other than the pitched rearward position; under these circumstances, then, the stimulation energy level will continue to decrease until a switch signal other than pitched rearward is sensed. The rate of continuous, incremental decrease in the stimulation energy level with the switch 78 in the pitched rearward position can be non-linear or linear over time as described above with respect to operation in the pitched forward position.

Step 310 relates to the switch signal (read at step 304) reflecting the switch 78 (FIG. 2) being depressed ("SELECT (press)"). If it is detected that the switch 78 has been pressed ("yes" at step 310), reference is made to the current setting of "Select_State" at step 324. If it is determined that the current Select_State setting is "Inactive" ("yes" at step 324), the "Select_State" value is changed to "Press" at step 326. Also, the "Select_Time" value is marked, meaning that a length of time the switch 78 is maintained in the pressed position begins to be recorded. Subsequently, the switch signal is again read at step 304. If the switch signal indicates that the switch 78 is no longer being pressed ("no" at step 310), reference is made to the Select_State designation at step 328. If the Select_State is "Press" ("yes" at step 328, recalling that the Select_State could previously be designated as "Press" at step 326), the control unit 20 (FIG. 1) is operated to cause an attached printer (not shown) to print out current information, such as information displayed on the monitor 32 (FIG. 1) at step 330. Alternatively, instead of prompting a print function, step 330 can prompt operation of a multitude of other functions associated with the control unit 20, such as printing the screen display of an image guided surgery piece of equipment, activation of or control over a separate stimulus probe, initiating a monitoring sequence, etc. Further, "Select_State" is re-set to "Inactive". In this manner, then, the control unit 20 can be prompted to print desired information (or perform the designated auxiliary function) by simply depressing and releasing the switch 78 regardless of a pitch or roll position.

Conversely, following step 326 above, if, following setting of the Select_State to "Press", the switch signal continues to indicate that the switch 78 (FIG. 2) is pressed ("yes" at step 310), at step 324 a determination is made that the "Select_State" is not "Inactive" ("no" at step 324). Under these circumstances, a confirmation is made at step 332 that the "Select_State" designation is "Press". If the Select_State designation is something other than "Press" ("no" at step 332), the switch signal is again read at step 304. If the Select_State designation is "Press" ("yes" at step 332), the current Select_Time value (i.e., the length of time the switch 78 has been continuously held in the pressed position) is compared to a predetermined "HOLD_TIME" threshold value (otherwise indicative of the length of time the switch 78 must remain depressed before an energy cessation action is taken) at step 334. If the Select_Time value does not exceed the "HOLD_TIME" value ("no" at step 334), no action is taken, and the switch signal is again read at step 304. If the Select_Time value exceeds the HOLD_TIME threshold value ("yes" at step 334), the control unit 20 (FIG. 1) operates to stop delivery of stimulation energy to the probe assembly 50 (FIG. 2) at step 336, meaning that stimulation by the stimulus probe 72 (FIG. 2) ceases. Further, the "Select_State" is assigned a "Zeroed" designation, and the switch signal is again read at step 304. Subsequently, once the switch signal indicates that the switch 78 is no longer in the pressed position (i.e., "no" at step 310), the "Select_State" is re-designated as "Inactive" at steps 338 and 340.

Finally, if the switch signal read at step 304 indicates that the switch 78 (FIG. 2) has been rolled left or right ("yes" at step 312), other actions can be taken as desired. This had been generically designated as "expanded functionality" at step 342.

It will be recognized that the flow diagram of FIG. 5 represents but one methodology for interpreting and acting upon signals from the probe assembly 50 (FIG. 2), and in particular the switch 78 (FIG. 2), in accordance with the present invention. A wide variety of other actions can be taken, and switch signals varying from those specifically described can be employed. Further, some of the functionality described in FIG. 5 (such responses to pressing of the switch and/or left or right rolled positions) can be eliminated. In a most basic form, the control unit 20, and in particular the stimulator circuitry and related programming, is adapted to receive signals from a remote switch provided on or by the probe assembly 50, and facilitate continuous increase or decrease in delivered stimulation energy in response to the switch signals over a series of discrete, incremental steps.

Figure 6:
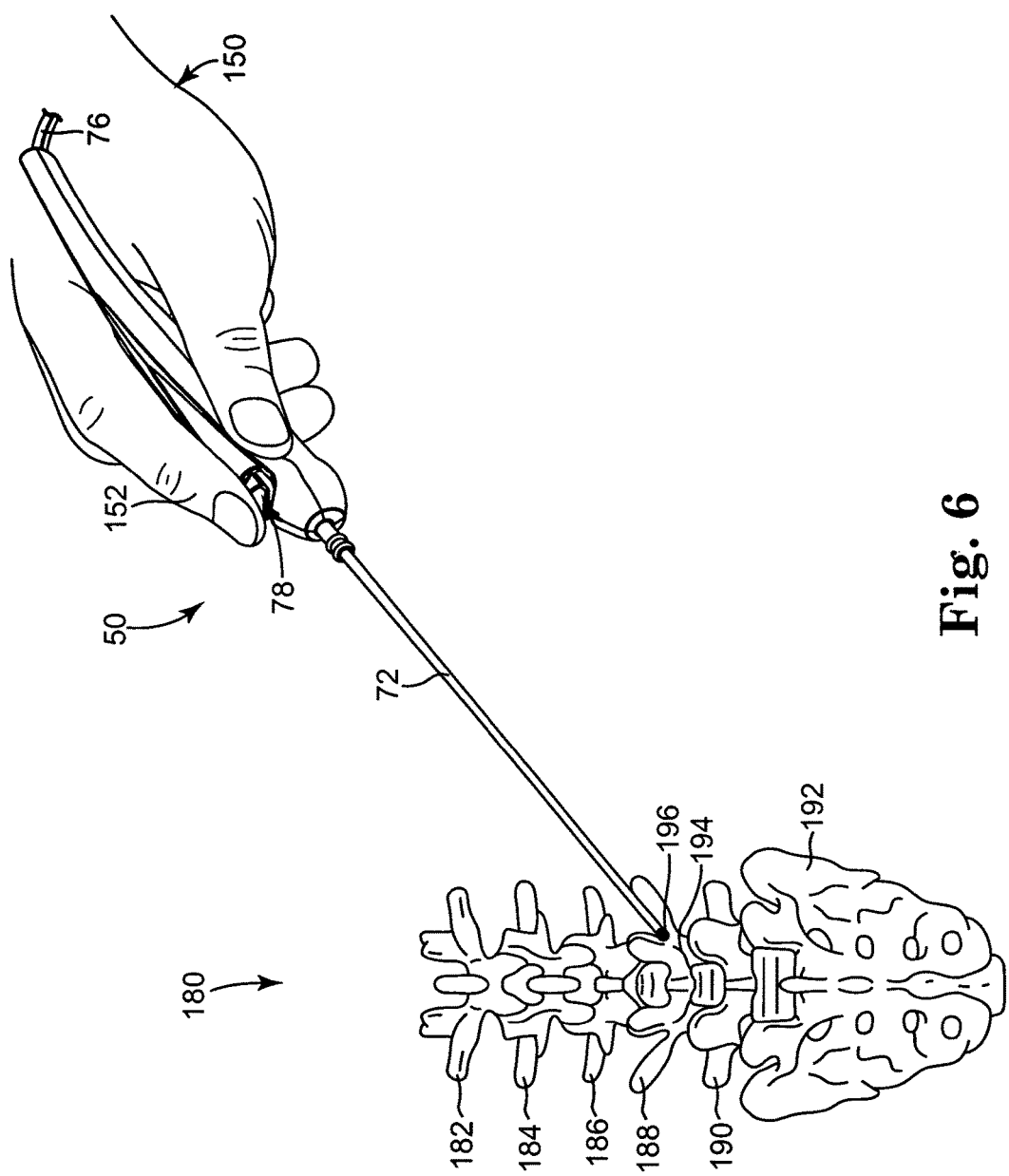
FIG. 6 illustrates one application of the evoked potential monitoring system in accordance with the present invention, including evaluating a pedicle hole.

One possible use of the probe assembly 50 employed as part of an evoked potential monitoring system is described with reference to FIG. 6. FIG. 6 depicts an enlarged posterior view of skeletal members of a lumbar spinal region 180 of a human patient. The lumbar spinal region 180 includes a first lumbar vertebra 182, a second lumbar vertebra 184, a third lumbar vertebra 186, a fourth lumbar vertebra 188, a fifth lumbar vertebra 190, and a sacrum 192 comprised of fused vertebrae. A pedicle 194 of the fourth lumbar vertebra 188 is provided with a pedicle hole 196 as part of a spinal stabilization procedure. The pedicle hole 196 is formed by the surgeon and may be tapped (i.e., threaded), or enlarged, as the surgical procedure indicates.

To evaluate placement of the pedicle hole 196, the evoked potential monitoring system 10 (FIG. 1) of the present invention can be employed. In one embodiment, sensing or recording electrodes (not shown) are placed on the patient at appropriate locations for sensing impulses (e.g., at or along muscles, the spinal column, peripheral nerves, etc.). Further, a ground electrode (not shown) is attached to the patient. The system 10 is then initiated. The surgeon manipulates the stimulator handpiece 70 and inserts the stimulus probe 72 into the pedicle hole 196. The surgeon can initiate electrical stimulation to the stimulus probe 72 by moving the switch 78. The stimulus level delivered to the stimulus probe 72 can be continuously incremented or decremented over a series of discrete, incremental steps by an appropriate movement of the switch 78, as best described with reference to FIG. 4A above. In addition, the surgeon can print the data ("print screen") from the monitor 32 (FIG. 1) or prompt a different feature by momentarily depressing the switch 78. In this regard, the monitor 32 visually indicates to the surgeon the stimulus levels, and other data, related to the stimulus probe 72.

During an exemplary evoked potential monitoring procedure, the surgeon selectively increments or decrements the stimulus level delivered to the stimulus probe 72 by pitching and/or rolling the switch 78 in the appropriate direction. For example, the surgeon can hold the switch 78 in the pitched forward position for a first period of time until the stimulation energy incrementally approaches a desired value. The surgeon can then briefly move to and release the switch 78 from the pitched forward position and/or pitched rearward position until the desired stimulation energy level is obtained. Following monitoring of the evoked potential at this stimulus level, the surgeon can, where desired, further increase the stimulation energy level by holding the switch 78 in the pitched forward position for another length of time, repeating the monitoring process. Finally, the surgeon can terminate the stimulus energy delivered to the stimulus probe 72 by depressing and holding the switch 78 for more than one second. In this manner, the surgeon can, remote of the control unit 20 (FIG. 1) continuously vary and control the electrical stimulation level delivered to, and thus by, the stimulus probe 72 over a series of discrete incremental steps via movement of the switch 78. Throughout the procedure, the evoked potential is monitored by the surgeon. If minimal or no reaction to the stimulation energy is sensed by the system 10, the surgeon can make a determination that the pedicle hole 196 is acceptable. Conversely, if an evoked potential is sensed by the system 10, the surgeon may determine that an alternative location for the pedicle hole 196 should be selected.

The pedicle hole evaluation procedure described above is but one possible application of the evoked potential monitoring system 10 (FIG. 1), and in particular the probe assembly 50, in accordance with the present invention. A multitude of other evoked potential monitoring procedures will equally benefit from the present invention. Examples of such procedures include, but are not limited to, monitoring the optic nerve, monitoring the extraocular nerves, monitoring the trigeminal nerve, monitoring the facial nerves (for example, as part of ear surgery), monitoring the cochlear nerve, monitoring the vagus nerve, monitoring the spinal accessory nerve, monitoring the hypoglossal nerve, spinal cord monitoring, monitoring the recurrent laryngeal nerve, thyroid and parathyroid gland surgery, etc., to name but a few.

FIG. 7 is a perspective view of an alternate probe assembly 200 in accordance with the present invention. The probe assembly 200 includes a stimulator handpiece 202 having a wheel switch 204. The wheel switch 204 is analogous to the joy stick-type switch 78 (FIG. 2) previously described is movable through a range of pitch and axial movements. In particular, the wheel switch 204 includes an actuator (not shown, but analogous to the actuator 115 (FIG. 3A) previously described) coupled to the control circuitry 112 (FIG. 2) within the stimulator handpiece 202 such that the pitch and axial movements of the switch 204 causes the actuator to signal the stimulator circuitry in the control unit 20 (FIG. 1) to remotely and continuously vary the stimulus level delivered to the stimulus probe 72 over a series of discrete, incremental steps, substantially as described above for the pitch and axial movements of the probe assembly 50 (FIG. 1).

FIG. 8 is a perspective view of another alternative embodiment probe assembly 210 in accordance with the present invention. The probe assembly 210 includes a stimulator handpiece 212 having a rocker switch 214. The rocker switch 214 is movable through a range of pitch and axial movements. In particular, the rocker switch 214 includes an actuator (not shown, but analogous to the actuator 115 of FIG. 3A) couple to the control circuitry 112 (FIG. 2) within the stimulator handpiece 212 such that the pitch and axial movements of the rocker switch 214 causes the actuator to signal the stimulator circuitry in the control unit 20 (FIG. 1) to remotely and continuously vary the stimulus level delivered to the stimulus probe 72 over a series of discrete, incremental steps, substantially as described above for the pitch and axial movements of the probe assembly 50 (FIG. 1).

Although specific embodiments of a stimulator handpiece for evoked potential monitoring have been illustrated and described, it will be appreciated by those of ordinary skill in the art that a variety of alternate and/or equivalent implementations could be substituted for the specific embodiments shown and described without departing from the scope of the present invention. Therefore, this application is intended to cover any adaptations or variations of stimulator handpieces and systems for evoked potential monitoring having a switch for the remote and continuous control of a stimulus level delivered to a stimulus probe. It is intended that this invention be limited only by the claims and the equivalents thereof.

What is claimed is:

1. An evoked potential monitoring system comprising:
a control unit including stimulator circuitry;
cabling including a control cable and an energy supply cable each independently electrically coupled to the control unit; and
a probe assembly electrically coupled to the control unit through the control cable, the probe assembly including:
a stimulus probe electrically coupled to the energy supply cable, and
a stimulator handpiece selectively maintaining the stimulus probe, the handpiece including:
a handle defining an enclosed region,
control circuitry disposed within the enclosed region and electrically connected to the stimulator circuitry through the control cable,
a switch electrically coupled to the control circuitry and extending from the enclosed region to an exterior portion of the handle, the switch movable to a plurality of positions, the handle fluidly sealed between the exterior portion to the enclosed region at the switch;
wherein the system is adapted such that movement of the switch to one of the plurality of positions relative to the handpiece remotely prompts the stimulator circuitry to continuously vary a stimulation energy level delivered to the stimulus probe while the switch is maintained in said one of the plurality of positions such that at least two different stimulation energy levels between 0.0 and 30.0 milliamperes are delivered.

2. The evoked potential monitoring system of claim 1, wherein the stimulus probe is a nerve probe.

3. The evoked potential monitoring system of claim 1, wherein the probe assembly is a monopolar probe assembly.

4. The evoked potential monitoring system of claim 1, wherein the probe assembly is a bipolar probe assembly.

5. The evoked potential monitoring system of claim 1, wherein the control unit is adapted to record a patient's response to stimulation energy delivered by the stimulus probe.

6. The evoked potential monitoring system of claim 1, wherein the system is adapted such that movement of the switch continuously varies the stimulation energy level delivered to the stimulus probe over a series of discrete, sequential steps.

7. The evoked potential monitoring system of claim 6, wherein the system is adapted such that the switch can be operated to select any of the discrete, incremental stimulation energy level steps available through the control unit.

8. The evoked potential monitoring system of claim 6, wherein the system is adapted to increment or decrement the stimulation energy level delivered to the stimulus probe in a non-linear fashion in response to movement of the switch.

9. The evoked potential monitoring system of claim 6, wherein the system is adapted to automatically increase or decrease the stimulation energy level delivered to the stimulus probe in a sequential fashion in response to movement of the switch.

10. The evoked potential monitoring system of claim 1, wherein the system is adapted such that movement of the switch increments the stimulation energy level delivered by the stimulus probe.

11. The evoked potential monitoring system of claim 1, wherein the system is adapted such that movement of the switch decrements the stimulation energy level delivered by the stimulus probe.

12. The evoked potential monitoring system of claim 1, wherein the stimulus probe is operable in a stimulating state and a non-stimulating state, and further wherein the system is adapted such that depressing and holding the switch ceases delivery of stimulation energy to the stimulus probe.

13. The evoked potential monitoring system of claim 1, further comprising an auxiliary device connected to the control unit, and further wherein the system is adapted such that depressing the switch causes the control unit to prompt operation of the auxiliary device.

14. The evoked potential monitoring system of claim 1, wherein the switch includes:
an actuator;
a post extending from the actuator; and
a pad coupled to the post.

15. The evoked potential monitoring system of claim 1, wherein the switch is configured to pitch longitudinally and roll laterally.

16. The evoked potential monitoring system of claim 1, wherein the switch is a pivoting rocker arm extending from the enclosed region to an exterior portion of the handle.

17. The evoked potential monitoring system of claim 1, wherein the switch is a finger wheel mounted within the enclosed region and extending to an exterior portion of the handle.

18. The evoked potential monitoring system of claim 1, wherein the switch has four degrees of freedom.

19. The evoked potential monitoring system of claim 1, wherein the switch has more than four degrees of freedom.

20. The evoked potential monitoring system of claim 1, wherein the switch is coupled to the handle.

21. The evoked potential monitoring system of claim 1, wherein the control circuitry includes a printed circuit board.

22. A stimulator handpiece for use with an evoked potential monitoring system, the handpiece comprising:
a handle defining an enclosed region;
a probe connector disposed within the enclosed region and configured to selectively receive a stimulus probe;
control circuitry disposed within the enclosed region and configured to electrically communicate with a control unit through a control cable; and
a switch electrically coupled to the control circuitry and extending to an exterior portion of the handle, the switch having at least three degrees of freedom for movement to a plurality of positions;
wherein movement of the switch to one of the plurality of positions remotely varies an electrical signal deliverable to the stimulus probe while the switch is maintained in said one of the plurality of positions such that at least two different stimulation energy levels are deliverable to the stimulus probe.

23. The stimulator handpiece of claim 22, wherein the switch includes:
an actuator;
a post extending from the actuator; and
a pad coupled to the post.

24. The stimulator handpiece of claim 23, wherein the post is moveable relative to the actuator.

25. The stimulator handpiece of claim 24, wherein the actuator is adapted to generate differing signals depending upon a position of the post relative to the actuator.

26. The stimulator handpiece of claim 22, wherein the switch is configured to pitch longitudinally and roll laterally.

27. The stimulator handpiece of claim 22, wherein the handpiece is characterized by a single switch.

* * * * *